(12) United States Patent
Anapliotis et al.

(10) Patent No.: US 8,518,122 B2
(45) Date of Patent: Aug. 27, 2013

(54) MODULAR JOINT PROSTHESIS

(75) Inventors: Emmanuel Anapliotis, Berlin (DE);
Curt Kranz, Berlin (DE); Martin Hilse,
Berlin (DE); Gunter Lob, Munich (DE)

(73) Assignee: Merete Medical GmbH, Berlin (DE)

( * ) Notice: Subject to any disclaimer, the term of this patent is extended or adjusted under 35 U.S.C. 154(b) by 0 days.

(21) Appl. No.: 13/120,628

(22) PCT Filed: Sep. 11, 2009

(86) PCT No.: PCT/DE2009/001272
§ 371 (c)(1),
(2), (4) Date: Mar. 23, 2011

(87) PCT Pub. No.: WO2010/034284
PCT Pub. Date: Apr. 1, 2010

(65) Prior Publication Data
US 2011/0196503 A1 Aug. 11, 2011

(30) Foreign Application Priority Data
Sep. 26, 2008 (DE) .......................... 10 2008 049 123

(51) Int. Cl.
*A61F 2/32* (2006.01)
(52) U.S. Cl.
USPC ....................................................... 623/22.42
(58) Field of Classification Search
USPC . 623/23.23, 23.28, 22.4–22.46, 23.11–23.14,
623/19.11–19.14, 18.11, 16.11, 20.14, 20.15;
606/79, 89, 95, 99
See application file for complete search history.

(56) References Cited

U.S. PATENT DOCUMENTS

| | | | | |
|---|---|---|---|---|
| 3,987,499 A | * | 10/1976 | Scharbach et al. | 623/17.11 |
| 4,578,081 A | * | 3/1986 | Harder et al. | 623/22.42 |
| 4,657,550 A | * | 4/1987 | Daher | 623/17.11 |

(Continued)

FOREIGN PATENT DOCUMENTS

| | | |
|---|---|---|
| DE | 33 40 767 A1 | 5/1985 |
| DE | 83 06 663 U1 | 7/1986 |

(Continued)

OTHER PUBLICATIONS

International Search Report for parent application PCT/DE2009/001272, having a mailing date of Feb. 10, 2010.

(Continued)

*Primary Examiner* — Alvin Stewart
(74) *Attorney, Agent, or Firm* — Andrus, Sceales, Starke & Sawall, LLP (57) ABSTRACT

The invention relates to modular joint prostheses, comprising a curved head part to the conical pins of which a slip-on joint ball is attached, and comprising a nail which can be inserted into the bone marrow canal of the long bone and has a nail neck, wherein a connecting means is provided between the head part and the nail neck which holds the head part in a non-rotatable manner. The connecting means comprises at least one collar-like module which is located in the axial direction of the nail and has at least two semi-shells, which are divided in the axial direction of the module, are detachably connected to each other, form an axially extending passage for inserting the nail head into the passage and have recesses for receiving a tensioning means, which in the tensioned state fixes the nail head in the passage exclusively by way of factional engagement.

15 Claims, 10 Drawing Sheets

(56) References Cited

U.S. PATENT DOCUMENTS

| | | | |
|---|---|---|---|
| 4,790,852 A * | 12/1988 | Noiles | 623/23.46 |
| 4,846,839 A * | 7/1989 | Noiles | 623/23.46 |
| 4,938,768 A * | 7/1990 | Wu | 623/23.47 |
| 5,032,130 A * | 7/1991 | Schelhas et al. | 623/22.42 |
| 5,352,227 A * | 10/1994 | O'Hara | 606/63 |
| 5,626,580 A * | 5/1997 | Brosnahan | 606/63 |
| 5,658,349 A | 8/1997 | Brooks et al. | |
| 5,906,644 A * | 5/1999 | Powell | 623/20.15 |
| 6,217,620 B1 * | 4/2001 | Park | 623/23.26 |
| 6,238,436 B1 * | 5/2001 | Lob et al. | 623/22.42 |
| 6,264,699 B1 * | 7/2001 | Noiles et al. | 623/23.23 |
| 6,299,648 B1 * | 10/2001 | Doubler et al. | 623/23.18 |
| 6,355,068 B1 * | 3/2002 | Doubler et al. | 623/22.42 |
| 6,428,578 B2 * | 8/2002 | White | 623/23.22 |
| 6,440,171 B1 * | 8/2002 | Doubler et al. | 623/22.42 |
| 6,454,810 B1 * | 9/2002 | Lob | 623/23.47 |
| 6,613,092 B1 * | 9/2003 | Kana et al. | 623/20.15 |
| 6,669,728 B2 * | 12/2003 | Despres et al. | 623/16.11 |
| 6,682,568 B2 * | 1/2004 | Despres et al. | 623/22.42 |
| 6,692,530 B2 * | 2/2004 | Doubler et al. | 623/22.42 |
| 6,699,293 B2 * | 3/2004 | White | 623/23.22 |
| 6,706,072 B2 * | 3/2004 | Dwyer et al. | 623/22.42 |
| 6,706,073 B2 * | 3/2004 | Draenert et al. | 623/22.46 |
| 6,786,932 B1 | 9/2004 | Blackmore | |
| 6,833,007 B2 * | 12/2004 | Lob | 623/23.47 |
| 6,866,683 B2 * | 3/2005 | Gerbec et al. | 623/18.11 |
| 7,435,263 B2 * | 10/2008 | Barnett et al. | 623/19.12 |
| 7,776,098 B2 * | 8/2010 | Murphy | 623/22.42 |
| 7,794,503 B2 * | 9/2010 | Daniels et al. | 623/22.11 |
| 7,998,218 B1 * | 8/2011 | Brown | 623/20.35 |
| 8,100,982 B2 * | 1/2012 | Heck et al. | 623/20.35 |
| 2004/0024469 A1 * | 2/2004 | Ferree | 623/23.26 |
| 2004/0199259 A1 * | 10/2004 | Pichon et al. | 623/22.42 |
| 2005/0004679 A1 * | 1/2005 | Sederholm et al. | 623/22.42 |
| 2005/0071014 A1 * | 3/2005 | Barnett et al. | 623/19.14 |
| 2009/0171463 A1 | 7/2009 | Brehm | |
| 2010/0241239 A1 * | 9/2010 | Smith | 623/22.42 |

FOREIGN PATENT DOCUMENTS

| | | |
|---|---|---|
| DE | 89 03 850 U1 | 6/1989 |
| DE | 196 33 865 A1 | 2/1998 |
| DE | 197 22 389 A1 | 12/1998 |
| DE | 20 2004 015578 U1 | 12/2004 |
| EP | 1 004 283 B1 | 5/2005 |
| EP | 1 529 493 A1 | 5/2005 |
| EP | 1 529 493 B1 | 6/2007 |
| FR | 2 670 108 A1 | 6/1992 |

OTHER PUBLICATIONS

International Search Report for parent application PCT/DE2009/001194, having a mailing date of Jan. 11, 2010.

* cited by examiner

MODULAR JOINT PROSTHESIS

CROSS-REFERENCE TO RELATED APPLICATIONS

This application is the U.S. national stage application of International Application No. PCT/DE2009/001272, filed Sep. 11, 2009, which International application was published on Apr. 1, 2010 as International Publication No. WO 2010/034284 A1 in the German language and which application is incorporated herein by reference. The International application claims priority of German Patent Application No. 10 2008 049 123.3, filed Sep. 26, 2008, which application is incorporated herein by reference.

The invention relates to a modular joint prosthesis having a curved head part, to the conical pin of which a slip-on joint ball is attached, and having a nail which can be inserted into the bone marrow canal of the long bone and has a nail neck, wherein between head part and nail neck a connecting means is provided which holds the head part in a non-rotatable manner.

The invention relates further to a modular joint prosthesis having a shaft-like shaped neck piece, to the conical pin of which a slip-on joint ball is attached, and having a nail which can be inserted into the bone marrow canal of the long bone and has a nail neck, wherein between neck piece and nail neck of the nail a connection means is provided which holds the neck piece in a non-rotatable manner in a predetermined angular position.

From DE 33 40 767 A1, an assembly set for a resection prosthesis having a head part and an end part is known, of which the one part has a conical pin and the other part has a conical bore, wherein between these two parts at least one intermediate part is provided which is adapted to pin and/or bore. The surfaces of the different parts abutting against each other when assembled can be secured against rotation by recesses which are adapted to each other.

This known prior art has the disadvantage that the prosthesis consists of a plurality of individual parts which requires a sustainable stock-keeping of these parts. In the assembled state, the individual parts must have the approximate shape of the curvature of the femur so that curvature and angular position which are suitable for the condition present in the respective patient can only be achieved through inventory holding of the adequate parts in order to restore the natural function of the joint to be replaced.

Furthermore, from EP 1 004 283 B1, an orthopedic prosthesis system for replacement of an articulating portion of a long bone is known which comprises a sleeve, a shaft, a neck and a connecting element. The connecting element has a connecting post which is formed with the shaft, has a proximal end provided with a thread, and a nut positioned in the neck.

This known teaching might be modularly designed for differently long shafts and sleeves; however, the connecting element itself does not have such modularity.

The fundamental disadvantage of all these known prostheses is that their lengths and angular positions are not adjustable whereby the modularity is significantly limited.

Furthermore, said known prosthesis system has the disadvantage that during a later revision, significant problems can occur when detaching the connecting means which act exclusively in the axial direction because the axial connecting means can only be axially detached and removed which, in turn, can entail an undesired extension of soft, muscle and tendon parts with associated traumatization. Also, apart from that, the tightening or loosening torque to be axially applied to the connecting means, in particular to the nail shafts, acts against a firm fit in the bone.

OBJECT OF THE INVENTION

In light of this prior art, the invention is based on the object to provide a modular joint prosthesis which increases the modularity of the prosthesis by increased length variability, allows an improved adjustability of the angular position while, at the same time, reducing the number of parts, and simplifies revision surgeries.

This object is solved by a modular joint prosthesis of the aforementioned type with the features of claim 1 or claim 2.

Advantageous configurations of the joint prosthesis derive from the sub-claims.

The solution according to the invention is characterized in that a modular joint prosthesis with a wide variety of uses, for example for the proximal femur, in case of resections due to metastases in the bone, infections or trauma can be provided, which offers a high variety of variations with a small number of parts and an improved adjustability of the angular position.

The transmission of the maximum physiological loads, in particular forces and torques, into the long bone is achieved with particular advantage in that the connecting means comprises at least one collar-like module which is arranged in the axial direction of the nail and has at least two half-shells which are divided in the axial direction of the module, are detachably connected to each other, form an axially extending passage with each other for inserting the nail neck into the passage, and have recesses which are arranged coaxially in the longitudinal direction of the module, are each positioned perpendicularly to the axis and correspond to each other, for receiving a tensioning means which, in the tensioned state, fixes the nail neck in the passage exclusively by means of frictional engagement in a jaw-like manner with a tightening torque sufficient to prevent axial displacement and rotation.

The transmission of the loads is also achieved in an advantageous manner by a neck piece of relatively short length which is formed at its distal end into a helmet-shaped receiving head which can be slipped onto the nail neck of the nail and has an insertion opening for inserting the nail neck or a connecting piece, wherein the receiving head is provided with a slot which runs in the direction of the longitudinal axis of the head part approximately as far as into the shaft and to which recesses are assigned which are each positioned perpendicularly to the axis and correspond to each other for receiving a tensioning means which, in the tensioned state, clampingly fixes the nail neck or the connecting piece in the receiving head of the head part exclusively by means of frictional engagement in a jaw-like manner with a tightening torque sufficient to prevent axial displacement and rotation. This ensures that a physiological force transmission into the femur can take place with optimal adaptation to the angular position of the conditions present in the patient.

The invention is based on the knowledge that a collar-like module which engages in a jaw-like manner on the nail shaft of the nail generates a frictional engagement between nail neck and passage which frictional engagement runs linearly along the circumference of the nail neck and reliably excludes an axial displacement and/or rotational movement of the parts involved in the connection, even in case of high loads. The linear contact excludes fretting at the contact points by the fact that reciprocating movements are prevented. The linearly acting frictional engagement is achieved by a profile provided on the inner wall of the passage, wherein the neck diameter of the nail is adapted to the inner diameter of the passage.

With the tensioning means which are arranged directly next to each other in the longitudinal direction of the module, the frictional engagement can be secured by an adequately high tightening torque. A sufficiently high tightening torque is generated by screwing hexagon socket screws with a torque wrench into the corresponding recess provided with an internal thread.

It is further of particular advantage that the jaw-like connection between the shaft of the nail on the one hand and the collar-like module or the receiving head on the other can be disengaged without any problems even during a revision and that the traumatization of the body tissue in the region of the joint can be, kept very low. This is achieved in particular by the particularly advantageous ventral accessibility of the tensioning means at the collar-like module formed from half-shells as well as at the slotted receiving head, whereby the surgical intervention is significantly simplified.

Due to the length variability of the module for different lengths, the joint prosthesis according to the invention is well adaptable to the different anatomical conditions in the individual patients. Due to the fact that the receiving head of the neck piece can be slipped onto the nail shaft of the nail and is retained in frictional engagement, it is also possible to continuously adjust the antetorsion angle and to keep the resection height to a minimum.

It is essential for the invention that the connecting means themselves are structured in a modular manner so that it is possible to take over the settings of an existing hip TEP and/or to combine components with different CCD angles.

Particular advantages are in particular achievable if modules of different or equal length are connected to each other by a module connector so that the length variability of the joint prosthesis according to the invention can be significantly increased.

The modular length variability of the joint prosthesis according to the invention can be increased according to an advantageous development of the invention by combining the module connector with the collar-like module so that the joint prosthesis can be assembled in different lengths in a modular manner. For connecting the module connector to the nail, in this case, in addition, a collar-like module is provided which has at least two half-shells which are divided in the axial direction of the module, are detachably connected to each other, form an axially extending passage with each other for inserting the nail neck into the one end and the module connector into the other end of the passage, and have recesses which are arranged coaxially in the longitudinal direction of the module, are each positioned perpendicularly to the axis and correspond to each other, for receiving a tensioning means which, in the tensioned state, clampingly fixes the nail neck in the passage exclusively by means of frictional engagement in a jaw-like manner with a tightening torque sufficient to prevent axial displacement and rotation.

In a further configuration of the invention, all parts of the joint prosthesis according to the invention have a rough surface to accelerate the ingrowth of the prosthesis in the surgically treated region.

In a further advantageous development of the invention, the outer diameter of the nail neck is adapted to the inner diameter of the passage in the connection module or the receiving head of the neck piece, wherein nails with different lengths and shaft lengths, but with the same diameter of the nail neck are provided.

All parts of the joint prosthesis according to the invention consist of a body-compatible and body-resistant, preferably metallic material, for example titanium, tantalum, niobium or their alloys.

Further advantages and details are apparent from the following description with reference to the attached drawings.

EXEMPLARY EMBODIMENTS

The invention is to be illustrated in more detail by means of two exemplary embodiments. In the figures.

EXAMPLE 1

Figure 1:
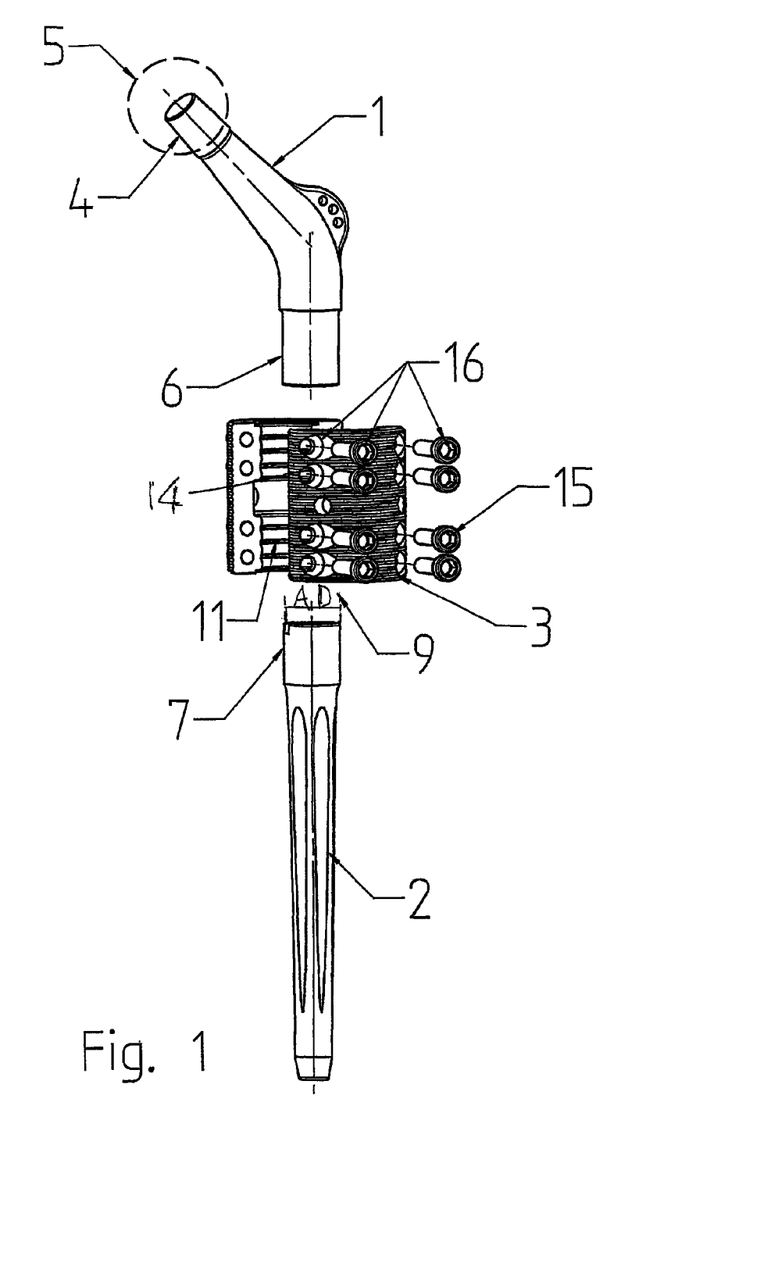
FIG. 1 shows an exploded illustration of the joint prosthesis according to the invention with a bent, long head piece.

FIG. 1 shows the basic structure of the joint prosthesis according to the invention in a first embodiment variant in an exploded illustration. The joint prosthesis according to the invention which is used, for example, in case of resections due to metastases in the bone, hip revisions or also in case of infections or trauma, is composed of a curved, one-piece head part 1 which is adapted according to the biomechanical conditions of the anatomy of the respective patient, a nail 2, for example femur nail, and a connection module 3. On the conical pin 4 of the head part 1, a slip-on joint ball 5 is arranged which engages with a non-illustrated joint socket. The distal end of the head part 1 is formed into a cylindrical shaft 6 from solid metal and is inserted into the connection module 3, which is described later, to be fastened therein.

The nail 2 is inserted into the bone marrow canal of the non-illustrated long bone and anchored therein. The nails 2 have different lengths and are anatomically adapted to the contour of the marrow canal in a suitable manner. They are sufficiently secured by locking screws or a star-shaped profile against rotation within the marrow canal.

Figure 2:
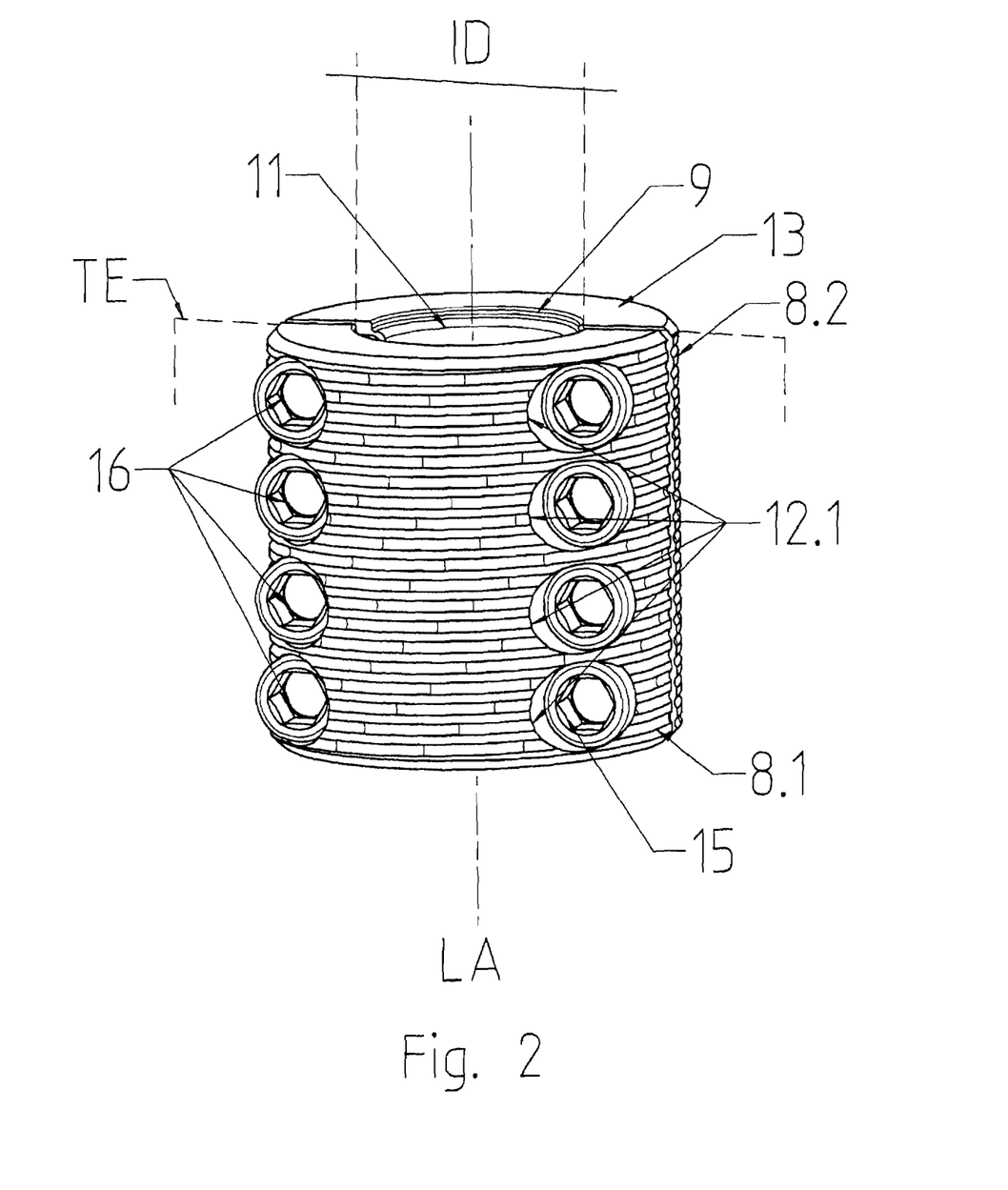
FIG. 2 shows a perspective view of a collar-like connection module for connecting nail shaft and head part.

The nail 2 has a cylindrical nail neck 7 made of solid metal. The shaft 6 of the head part 1 is rigidly connected to the nail 2 by means of the connection module 3 which encompasses the nail neck 7 and the shaft 6 in each case in a collar-like manner. The connection module 3—as shown in FIG. 2—is made of two pieces and consists of two cylindrical half-shells 8.1 and 8.2 which are formed in a substantially similar manner. Both half-shells 8.1 and 8.2 define in the assembled state a passage 9, the inner wall 10 of which has a profile 11 arranged perpendicularly to the longitudinal axis LA of the module. In each case four adjacent recesses 12.1 and 12.2 are incorporated in each of the half-shell walls 13 in such a manner that the recesses are arranged coaxially to the longitudinal axis LA of the module 3 and perpendicularly to the virtually extending dividing plane TE so that, for example, at least 8 recesses belong to the connection module 3. In the recesses 12.1 of the half-shell 8.2, an internal thread 14 is incorporated into which a hexagon socket screw 15 can be screwed which is inserted through the recess 12.1 of the half-shell 8.1.

The half-shells 8.1 and 8.2 together with the respective hexagon socket screw 15 internal thread 14 corresponding thereto form a jaw-like tensioning means 16 which, when tightening the hexagon socket screw 15, abuts circumferentially against the cylindrical nail neck 7 and generates a plurality of circumferentially extending linear frictionally engaged connections between the profile 11 and the nail neck 7. The outer diameter AD of the nail neck 7 is suitably adapted to the inner diameter ID of the passage 9.

The resistance of said frictionally engaged connection against axial displacement or rotation of the components can be very accurately and exactly set by applying a defined tightening torque to the hexagon socket screw 14. By allocating in each case four tensioning means 16 to the nail neck 7, a secure connection between nail 2 and head part 1 is achieved.

All tensioning means 16 are aligned in a ventral direction and thus are accessible from the outside without any problems during a later revision, without the need to have to traumatize larger regions of the body's own tissue.

Figure 3:
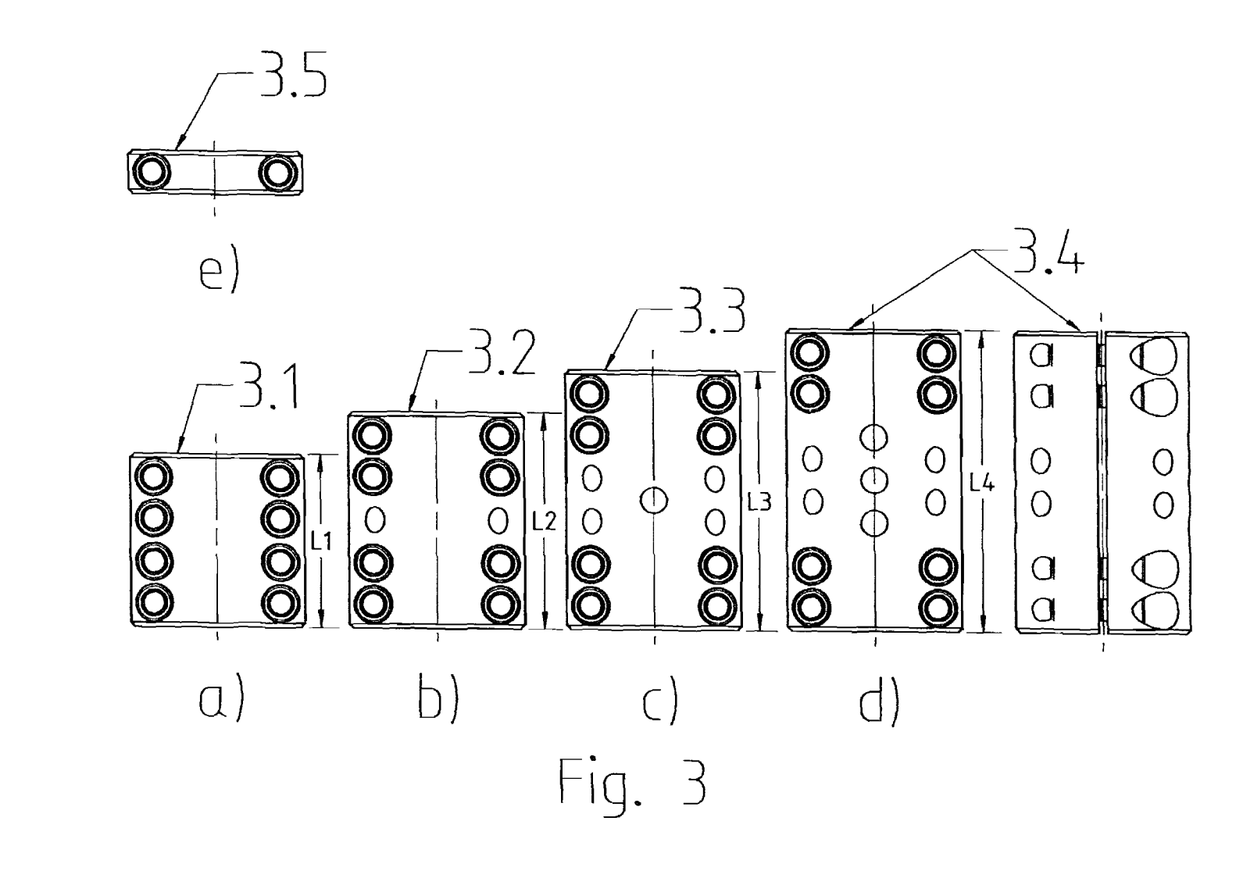
FIGS. 3a to 3e show a top view of different connection modules of an assembly set with different lengths.

FIGS. 3a to 3d show different connection modules 3.1 to 3.4 with a lengths L, for example a connection module 3.1 with a length L1 (FIG. 3a), a connection module 3.2 with a length L2 (FIG. 3b), a connection module 3.3 with a length L3 (FIG. 3c), and a connection module 3.4 with a length L4 (FIG. 3d). It is to be understood that also the lengths of the connection modules can be selected according to the anatomical conditions of the respective patients.

Figure 4:
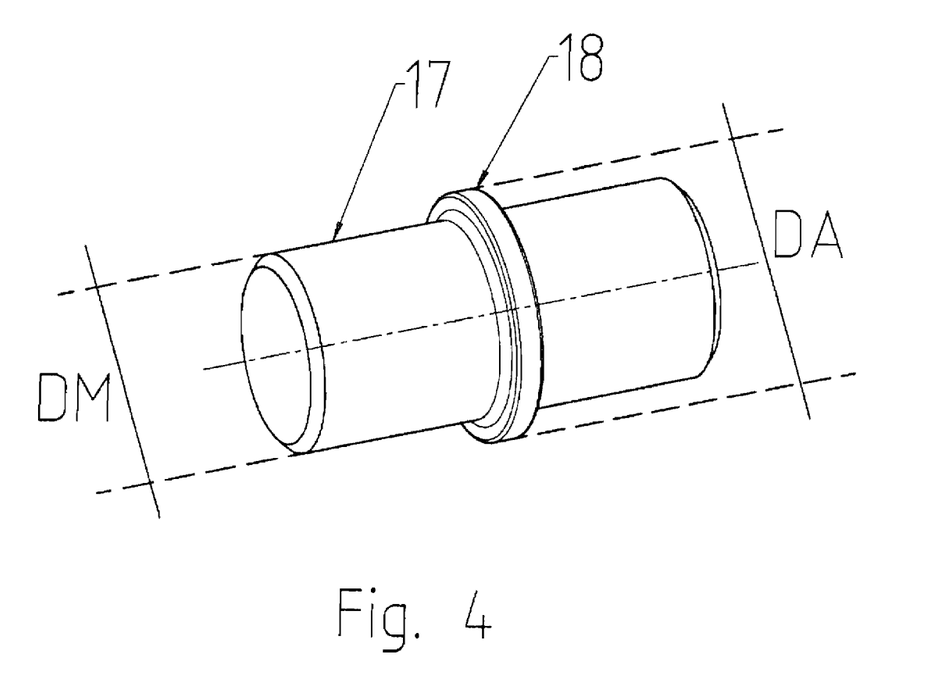
FIG. 4 shows a perspective view of a module connector.

FIG. 4 shows a module connector 17 which is shaped like a round bar and by means of which differently long or equally long connection modules 3.1 to 3.4 can be joined together. The module connector 17 consists of solid material, the diameter DM of which is adapted to the inner diameter ID of the passage 9. The module connector 17 has a centrally arranged circumferential limit stop 18 with a diameter DA which is larger with respect to the inner diameter ID of the passage 9. By inserting the respective ends of the module connector 17 into the respective end of the passage 9 of the connection modules 3.1 to 3.4 to be connected in each case and tensioning each of the associated tensioning means 16, a frictionally engaged connection is generated between the module connector 17 and the connection modules.

Thereby it is possible to combine the individual connection modules 3.1 to 3.4 with each other and to achieve a high length variability.

Figure 5:
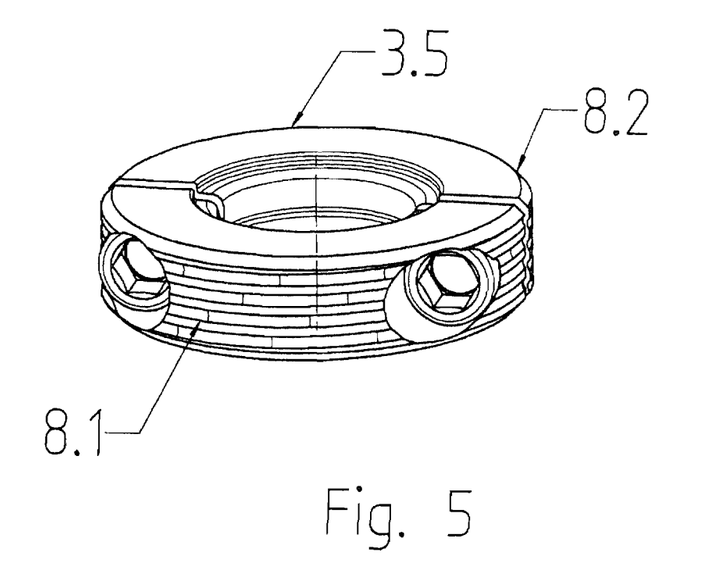
FIG. 5 shows a perspective view of a stop or support module.

The limit stop or support module 3.5 shown in the FIGS. 3e and 5 serves as a height-adjustable support with respect to the long bone, for example femur.

EXAMPLE 2

Figure 6:
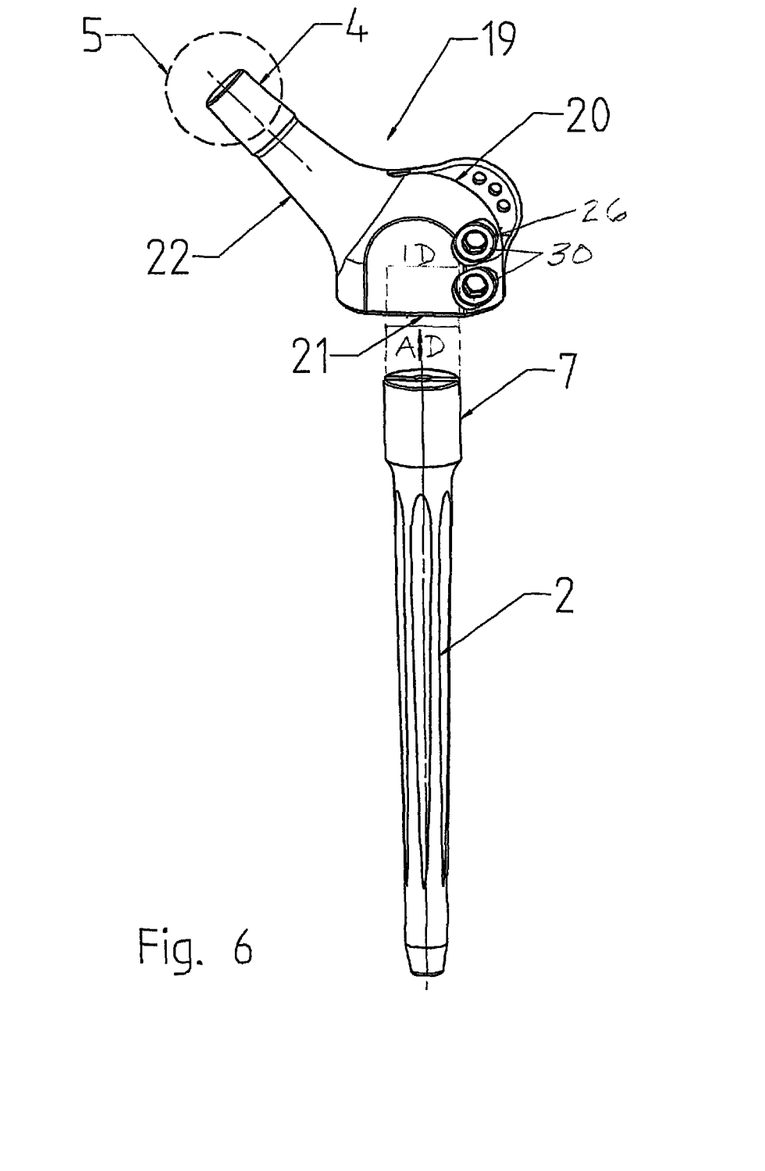
FIG. 6 shows an exploded illustration of a further variant of the joint prosthesis according to the invention having a short neck piece with receiving head.

FIG. 6 shows a further variant of the joint prosthesis according to the invention in an exploded illustration. This joint prosthesis comprises a shaft-like neck piece 19 of relatively short length and a nail 2, for example femur nail. The essence of this variant of the invention is that the connection module 3, which in example 1 is still a separate part, becomes an integral part of the shaft-like neck piece 19 so that a total of only two elements form the joint prosthesis according to the invention.

As in example 1, the neck piece 19 has a conical pin 4 onto which a slip-on joint ball 5 is arranged which engages with a non-illustrated joint socket. The distal end of the neck piece 19 is formed into a helmet-like receiving head 20 which has an insertion opening 21 for inserting the nail neck 7. The receiving head 20 is provided with a slot 23 which runs in the direction of the longitudinal axis LA of the head part 19 approximately as far as into the shaft 22 of the neck piece 19. In the side walls 24, in each case two recesses 25.1 and 25.2 are assigned to the slot 23 which recesses are positioned perpendicularly to the longitudinal axis LA and correspond to each other and serve for receiving a tensioning means 26 so that also the antetorsion angle can be continuously adjusted.

Figure 7A:
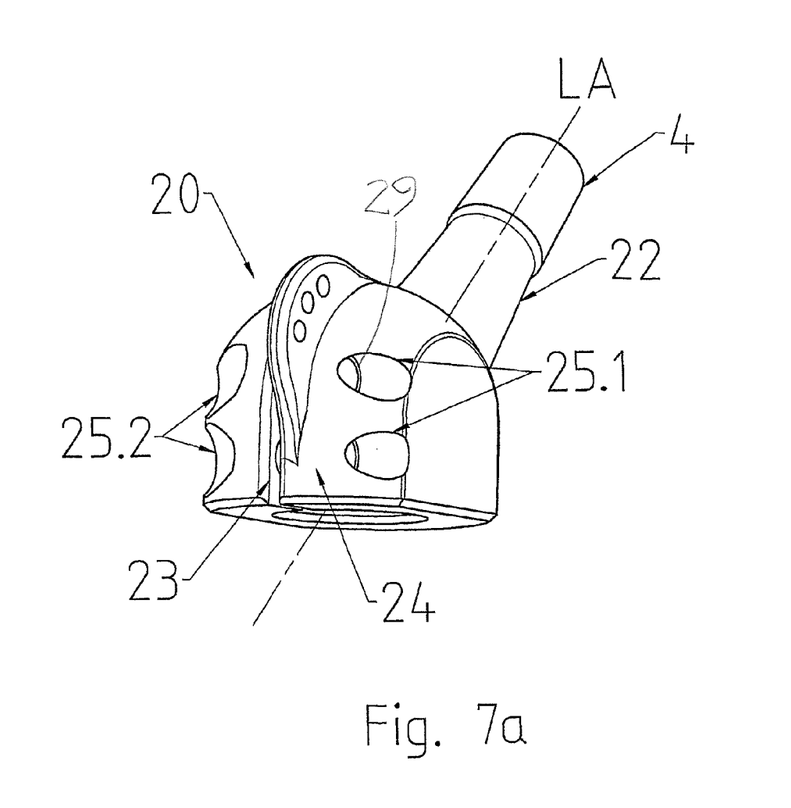
FIGS. 7a to 7c show perspective views of the receiving head according to FIG. 6, and FIGS. 8a to 8c show a view of the nails with different lengths.
Figure 7B:
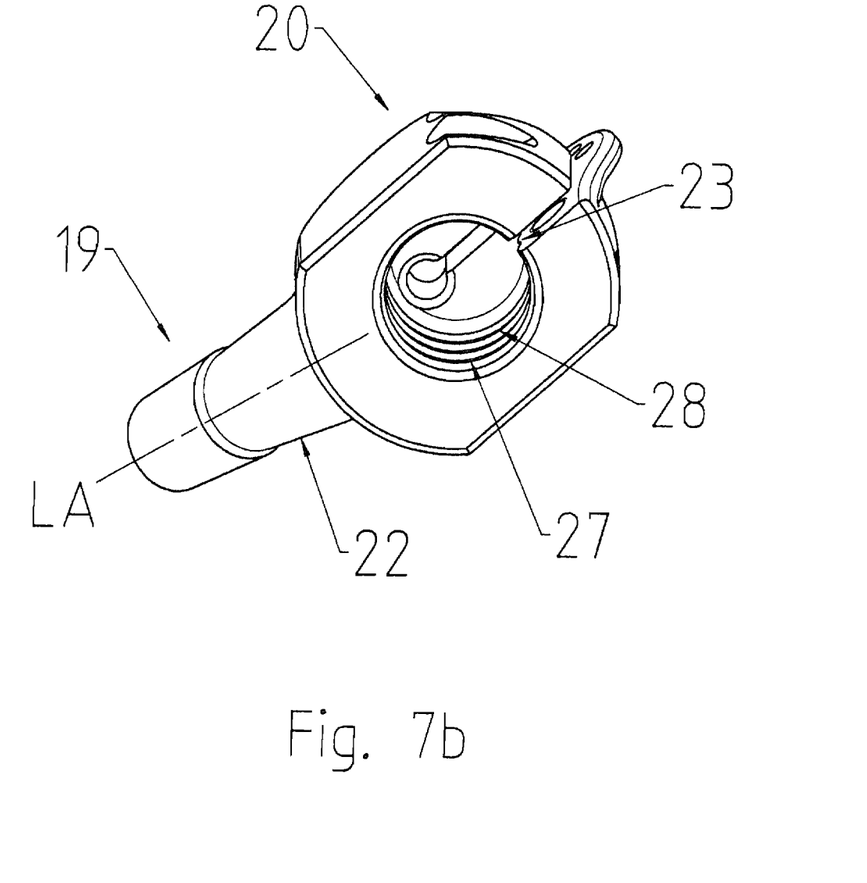

The inner wall 27 of the receiving head 20 is provided with a profile 28 arranged perpendicularly to the longitudinal axis LA of the neck piece 19 (see FIGS. 7a and 7b).

In the recesses 25.1 and 25.2 of the side walls 24, an internal thread 29 is incorporated into which a hexagon socket screw 30 can be screwed which is inserted through the recess 25.1.

Figure 7C:
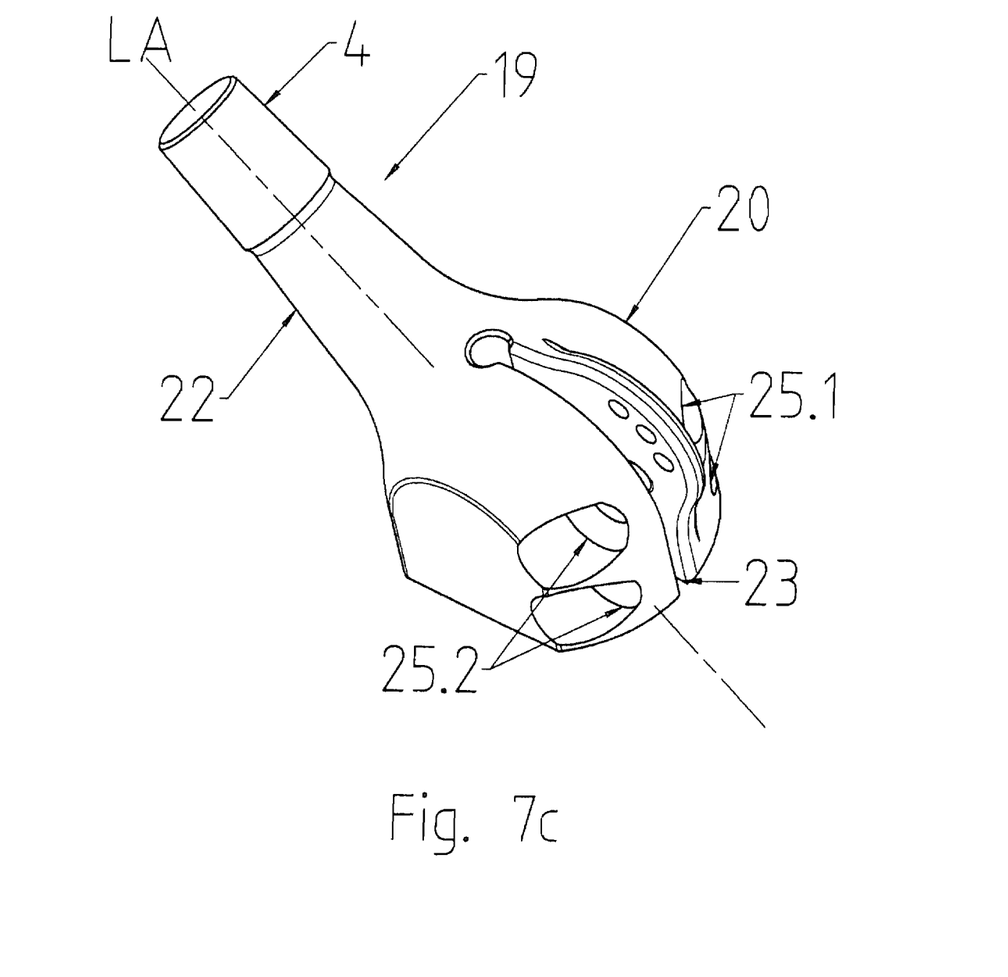

The recesses 25.1 and 25.2 with their internal threads 28 together with the respective hexagon socket screw 30 and the slot 23 form the jaw-like tensioning means 26 which, when tightening the hexagon socket screw 30, abuts circumferentially against the cylindrical nail neck 7 and generates a plurality of circumferentially extending linear frictionally engaged connections between the profile 28 and the nail neck 7. The outer diameter AD of the nail neck 7 is suitably adapted to the inner diameter ID of the insertion opening 21.

The resistance of said frictionally engaged connection against axial displacement or rotation of the components can be very accurately and exactly set by applying a defined tightening torque to the hexagon socket screw 15. By allocating in each case four tensioning means 16 to the nail neck 7, a secure connection between nail 2 and head part 1 is achieved.

All tensioning means 26 are aligned in a ventral direction and thus are accessible from the outside without any problems during a later revision, without the need to have to traumatize larger regions of the body's own tissue.

Of course, it also belongs to the solution according to the invention if the module connector 17 illustrated in FIG. 4, the outer diameter DA of which is adapted to the insertion opening 21, is inserted into the insertion opening 21 of the receiving head 20 and an increased length variability of the joint prosthesis is achieved in that the nail neck 7 of the nail 2 and the module connector 17 are connected by differently long connection modules 3 (see FIGS. 3a-d).

Figure 8:
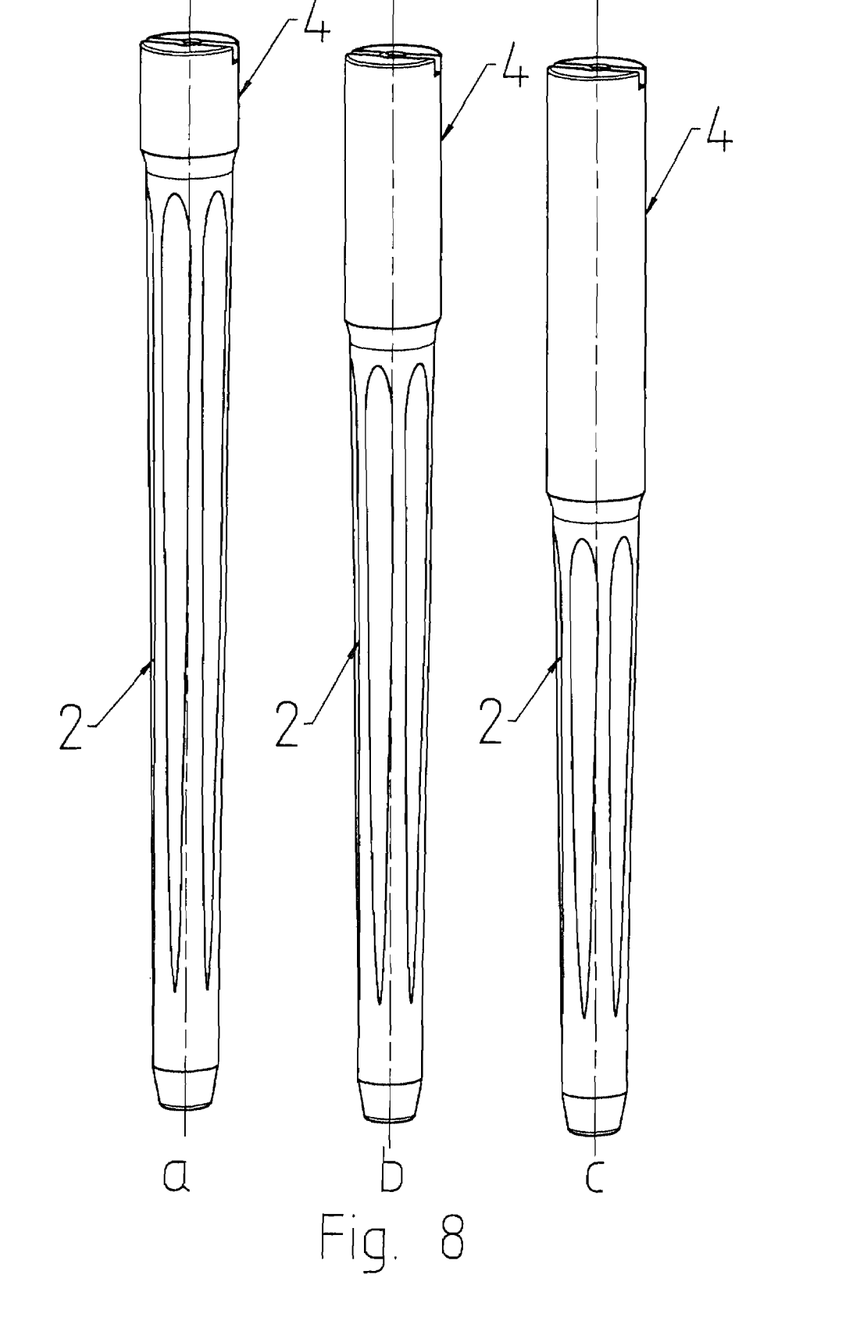

FIGS. 8a to c show examples of nails of different length, the neck diameter AD of which is adapted to the inner diameter ID of the passage 9 of the respective connection modules 3.1 to 3.4 or the insertion opening 21 in the receiving head 20.

All parts of the joint prosthesis according to the invention consist of a body-compatible and body-resistant metallic material. The outer surfaces are provided with a defined roughness, for example between 20 μm and 80 μm. This has the purpose, on the one hand, to increase the friction coefficient of the frictionally engaging partners and, on the other, to facilitate the ingrowth of the implant.

The configuration of invention is not limited to the aforementioned exemplary embodiments. Rather, variants are conceivable which can deviate from the illustrated solution also in case of fundamentally different configurations.

| Reference number list | |
| --- | --- |
| Head part | 1 |
| Nail | 2 |
| Connection module | 3, 3.1-3.4 |
| Support or limit stop module | 3.5 |
| Pin of 1 | 4 |
| Joint ball | 5 |
| Cylindrical shaft of 1 | 6 |

-continued

| Reference number list | |
|---|---|
| Nail neck of 2 | 7 |
| Half-shells of 3 | 8.1, 8.2 |
| Passage in 3 | 9 |
| Inner wall of 3 | 10 |
| Profile | 11 |
| Recesses | 12.1, 12.2 |
| Half-shell wall | 13 |
| Internal thread | 14 |
| Hexagon socket screw | 15 |
| Tensioning means | 16 |
| Module connector | 17 |
| Limit stop of 17 | 18 |
| Shaft-like neck piece | 19 |
| Receiving head | 20 |
| Insertion opening in 20 | 21 |
| Shaft of 19 | 22 |
| Slot | 23 |
| Side walls of 19 | 24 |
| Recess | 25.1, 25.2 |
| Tensioning means | 26 |
| Inner wall of 19 | 27 |
| Profile | 28 |
| Internal thread | 29 |
| Hexagon socket screw | 30 |
| Outer diameter of 18 | DA |
| Diameter of 17 | DM |
| Inner diameter of 9 | ID |
| Length of 3, 3.1-3.4 | L |
| Longitudinal axis of 3, 3.1-3.4 | LA |
| Dividing plane of 3 | TE |
| 10 drawings | |

The invention claimed is:

1. A modular joint prosthesis comprising:
a head part having a first end comprising a shaft, a curved middle portion, and a second, opposite end comprising a pin to which a slip-on joint ball can be attached,
a nail which can be inserted into a bone marrow canal of a long bone, the nail having a nail neck, and
a connecting means provided between the head part and the nail neck, the connecting means holding the head part in a non-rotatable manner,
wherein the connecting means comprises at least one collar-like module which is arranged in an axial direction of the nail and has at least two half-shells which,
are divided in an axial direction of the module,
are detachably connected to each other,
form an axially extending passage with each other, a first end of the passage for receiving the nail neck into the passage, and a second, opposite end of the passage for receiving the shaft of the head part into the passage, and
have recesses which are aligned coaxially with each other in a longitudinal direction of the module, are each positioned perpendicularly to a longitudinal axis and receive a tensioning means which, in the tensioned state, fixes the nail neck and the shaft of the head part in the passage by frictional engagement in a jaw-like manner with a tightening torque sufficient to prevent axial displacement and rotation, and
wherein only the shaft of the head part is received within the second end of the passage such that the head part can be rotated with respect to the module when the tensioning means is in an un-tensioned state.

2. The joint prosthesis according to claim 1, wherein the module has a substantially cylindrical shape.

3. The joint prosthesis according to claim 1, wherein the module is variable in length by combining modules with different lengths with each other.

4. The joint prosthesis according to claim 1, further comprising a module connector for connecting modules of the same or different length (L), wherein an outer diameter (AD) of the module connector corresponds to an inner diameter (ID) of the passage.

5. The joint prosthesis according to claim 1, wherein the passage has a profile on an inner wall thereof, the profile arranged transversely to the longitudinal direction (LA) of the module and providing linear frictional engagement with a circumference of the nail neck so as to prevent movement between the nail neck and the module.

6. The joint prosthesis according to claim 1, wherein the module comprises a plurality of modules having different lengths (L) and equal diameters.

7. The joint prosthesis according to claim 1, wherein a neck diameter (AD) of the nail corresponds to an inner diameter (ID) of the passage.

8. The joint prosthesis according to claim 1, wherein the tensioning means consist of a hexagon socket screw and an internal thread provided in the corresponding recess.

9. The joint prosthesis according to claim 8, wherein the tensioning means is secured against loosening by applying a specified tightening torque.

10. The joint prosthesis according to claim 1, wherein the nail has different lengths (L), and wherein the diameter of the nail neck of the nails of different lengths is equal.

11. The joint prosthesis according to claim 1, wherein all parts of the prosthesis consist of a biocompatible alloy.

12. The joint prosthesis according to claim 11, wherein the biocompatible alloy is a titanium alloy.

13. The joint prosthesis according to claim 1, wherein all parts of the prosthesis have a rough surface for facilitating the growth of the bone thereon.

14. A modular joint prosthesis comprising:
a curved head part, to which a slip-on joint ball can be attached, and
a nail which can be inserted into a bone marrow canal of a long bone and has a nail neck,
wherein between the head part and the nail neck, a connecting means is provided which holds the head part in a non-rotatable manner,
wherein the connecting means comprises at least one collar-like module which is arranged in an axial direction of the nail and has at least two half-shells which,
are divided in an axial direction of the module,
are detachably connected to each other,
form an axially extending passage with each other for inserting the nail neck into the passage,
have recesses which are aligned coaxially with each other in a longitudinal direction of the module, are each positioned perpendicularly to a longitudinal axis and receive a tensioning means which, in the tensioned state, fixes the nail neck in the passage by frictional engagement in a jaw-like manner with a tightening torque sufficient to prevent axial displacement and rotation, and
wherein the module is variable in length by combining modules with different lengths with each other.

15. A modular joint prosthesis comprising:
a curved head part, to which a slip-on joint ball can be attached, and
a nail which can be inserted into a bone marrow canal of a long bone and has a nail neck,
wherein between the head part and the nail neck, a connecting means is provided which holds the head part in a non-rotatable manner, wherein the connecting means comprises at least one collar-like module which is arranged in an axial direction of the nail and has at least two half-shells which,
are divided in an axial direction of the module,
are detachably connected to each other,
form an axially extending passage with each other for inserting the nail neck into the passage,
have recesses which are aligned coaxially with each other in a longitudinal direction of the module, are each positioned perpendicularly to a longitudinal axis and receive a tensioning means which, in the tensioned state, fixes the nail neck in the passage by frictional engagement in a jaw-like manner with a tightening torque sufficient to prevent axial displacement and rotation, and
wherein the joint prosthesis further comprises a module connector for connecting modules of the same or different length (L), wherein an outer diameter (AD) of the module connector corresponds to an inner diameter (ID) of the passage.

* * * * *